United States Patent [19]

Rubin

[11] 4,257,415

[45] Mar. 24, 1981

[54] PORTABLE NEBULIZER TREATMENT APPARATUS

[76] Inventor: Howard Rubin, 1937 Nester St., Philadelphia, Pa. 19115

[21] Appl. No.: 36,320

[22] Filed: May 7, 1979

[51] Int. Cl.³ .......................................... A61M 16/00
[52] U.S. Cl. ........................ 128/200.21; 128/203.12; 128/205.12; 128/204.21; 128/205.18
[58] Field of Search .................... 128/205.18, 200.17, 128/200.18, 200.21, 200.22, 204.21, 204.25, 205.12, 205.13, 205.24, 205.25, 203.12; 200/42 R, 51 R

[56] References Cited

U.S. PATENT DOCUMENTS

| Re. 29,613 | 4/1978 | Kropfhammer | 128/909 X |
|---|---|---|---|
| 2,449,165 | 9/1948 | Heidbrink | 128/200.13 |
| 3,301,255 | 1/1967 | Thompson | 128/200.18 |
| 3,370,137 | 2/1968 | O'Connor | 200/42 R |
| 3,379,194 | 4/1968 | Ziermann | 128/200.18 |
| 3,453,591 | 7/1969 | Perez | 200/42 R |
| 3,613,677 | 10/1971 | Blasko | 128/204.21 |
| 3,981,302 | 9/1976 | Veit | 128/202.26 |
| 3,990,442 | 11/1976 | Patneau | 128/200.14 |
| 4,019,511 | 4/1977 | Choporis et al. | 128/203.26 |
| 4,037,994 | 7/1977 | Bird | 417/316 |
| 4,076,021 | 2/1978 | Thompson | 128/205.18 |
| 4,080,103 | 3/1978 | Bird | 417/3 |

*Primary Examiner*—Henry J. Recla
*Attorney, Agent, or Firm*—Weiser, Stapler & Spivak

[57] ABSTRACT

An apparatus for providing nebulizer treatments to a patient, including during ambulatory periods. The apparatus, which is portable and lightweight, includes a case, which case is internally provided with a compressor, capable of battery operation, which supplies compressed air to a nebulizer. The nebulizer is adapted to contain a medication which is atomized for inhalation by a patient through a mouthpiece or a facemask. The apparatus is sufficiently small and lightweight to be carried by a patient during ambulatory periods.

7 Claims, 2 Drawing Figures

PORTABLE NEBULIZER TREATMENT APPARATUS

BACKGROUND OF THE INVENTION

This invention relates to the treatment of patients having respiratory ailments, and in particular to an apparatus which is capable of providing a nebulized medication to such patients.

In the treatment of patients having various respiratory ailments, particularly those having chronic obstructive lung diseases, various methods may be used.

Often, a fluid (air or other oxygen based medium) is provided to the patient under pressure. Such positive pressure breathing devices may be intermittent in nature, or may operate on a continuous basis. Such devices are generally cumbersome, and relatively complex in operation. A commonly known example of such a device is the iron lung. Many smaller devices exist as well.

In many applications, in addition to positive pressure, treatment is provided to a patient by introducing a nebulized medication into the lungs of the patient, during operation of the positive pressure breathing apparatus. This is accomplished by supplying a fluid, generally air, to an apparatus which atomizes, or nebulizes, a medication placed into that apparatus. The nebulized medication is then drawn into the lungs of the patient during inhalation, natural or assisted.

In general, devices capable of performing the foregoing were cumbersome, heavy, and difficult to operate, often relegating their use to a hospital environment, or at least to trained personnel on an outpatient basis. This has forced a patient suffering from a disease requiring the use of such equipment, to remain in a relatively stationary environment. Ambulatory periods were often not permitted, or at least inadvisable.

Recognizing this problem, workers skilled in the art to which this invention pertains have worked to develop devices of the foregoing type which are portable in nature. Examples of such devices may be found in U.S. Pat. Nos. 4,076,021; 3,990,442; and 3,301,255.

Although the foregoing devices are said to be portable, they are still too heavy to be carried about by a patient suffering from a respiratory ailment. Therefore, none of the devices illustrated permit a patient complete freedom of movement. Consequently, a patient is still prevented from freely moving about for any extended period of time.

Moreover, each of the foregoing devices specifically calls for the use of positive pressure in the treatment of a patient. However, it has recently been determined that, in many instances, positive pressure is counterproductive to the treatment of a patient. Positive pressure has been found to increase venus return, which forces the heart to work harder, even during the treatment process. Allowing a patient to freely inhale a nebulized medication, in the course of the natural breathing process, has been found to produce improved results in such cases. A better distribution of the medication through the lungs of the patient is afforded.

Thus, the prior art has not provided a respiratory treatment apparatus which is sufficiently light in weight, and which is sufficiently simple, effective and fail-safe in use, to permit a patient to be fully and independently ambulatory.

SUMMARY OF THE INVENTION

This invention relates to the treatment of patients having respiratory ailments, and in particular to an apparatus which is capable of providing a nebulized medication to a patient in a safe and effective manner, and which is sufficiently light in weight, simple in operation, and fail-safe to permit that patient to be fully and independently ambulatory.

In accordance with the present invention, a treatment apparatus is provided having a compressor, which compressor is preferably battery operated, and which supplies a fluid, generally air, to a nebulizer. The nebulizer is provided with a medication, which, responsive to the application of compressed air to that nebulizer, is atomized to form a vapor containing the medication. The nebulized medication is then applied to the patient, using a mouthpiece or a face mask, and is drawn by natural respiration, (inhalation) into the lungs of the patient.

The above apparatus is fitted to a case which is particularly adapted to make the apparatus light in weight, easy to use, and fail-safe in operation.

The combination of the apparatus including its case is sufficiently light in weight to permit it to be carried by a patient during his or her movements. Moreover, the case is sufficiently small, and conventional in appearance with respect to its outward features, in order to be as unobstrusive as possible.

Should treatment suddenly or unexpectedly become necessary, the apparatus is quickly assembled for operation, and is even adapted for use during the continued ambulation of the patient, toward an ultimate destination.

In this manner the patient is provided with a sense of security in movement which could not be provided using treatment devices of the prior art. The freedom and confidence such a system affords is beneficial to the psychological outlook of the patient as well.

Accordingly, it is an object of the present invention to provide an apparatus for the treatment of respiratory ailments which permits a patient to be freely and independently ambulatory.

It is another object of the present invention to provide an apparatus for the treatment of respiratory ailments which is sufficiently light in weight and sufficiently self contained in operation to be portable.

It is another object of the present invention to provide an apparatus for the treatment of respiratory ailments which is easy to use and substantially fail-safe in operation.

It is another object of the present invention to provide an apparatus for the treatment of respiratory ailments which is as unobtrusive in appearance as possible.

It is another object of the present invention to provide an apparatus for the treatment of respiratory ailments which has all of the foregoing advantages, and which is capable of providing a nebulized medication to a patient during ambulatory periods.

These objects and others will become apparent to those skilled in the art from the following disclosure of the preferred embodiment of the invention taken in conjunction with the drawings provided in which like reference characters refer to similar parts throughout the several views provided, in which:

DESCRIPTION OF THE PREFERRED EMBODIMENT OF THE INVENTION

Figure 1:
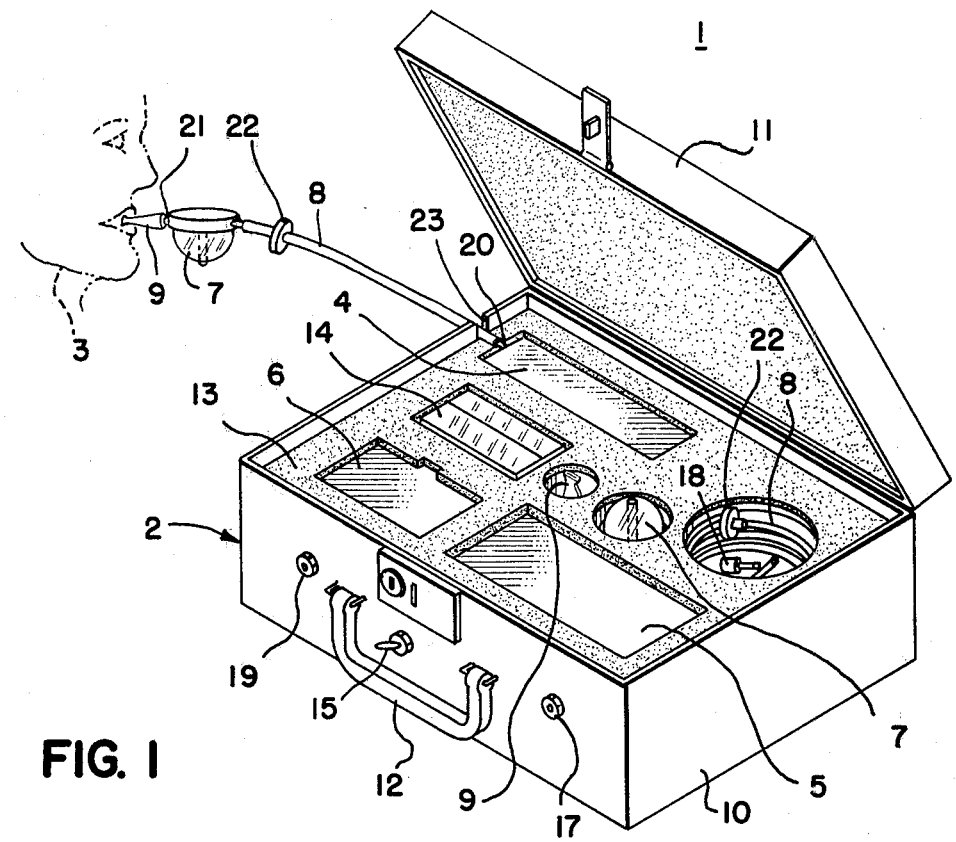
FIG. 1 is an isometric view of a preferred embodiment of the treatment apparatus of the present invention.

Although specific terms are used in the following description for the sake of clarity, these terms are intended to refer only to the particular structure of the invention selected for illustration in the drawings, and are not intended to define or limit the scope of the invention.

Referring now to the drawings, there is shown in FIG. 1 a preferred embodiment of the nebulizer treatment apparatus 1 of the present invention.

The apparatus 1 generally comprises a case 2 which contains the implements used to provide treatments to patient 3. These implements generally include a motor operated compressor 4, a battery 5, a battery charger 6, a nebulizer 7, a quantity of tubing 8, and mouthpiece 9.

Case 2 may be constructed of any material which is sufficiently strong to provide a safe environment for the implements it contains, including wood, plastic, fiber board, or the like. Case 2 is provided with a main body section 10 and lid 11. In order for the case 2 to be as unobtrusive as possible, it is generally preferred that its shape be similar to that of a conventional brief case, valise, handbag, etc, and at least outwardly, that it give the appearance of such items. A handle 12 is provided to permit the case 2 to be easily carried by patient 3.

Positioned within the body section 10 of case 2 is a template 13 which houses the various elements of the treatment apparatus. Template 13 is preferably formed of a shock absorbing material in order to protect the elements of the system as they are carried. A foamed plastic has been found to provide excellent results, and is preferred in view of its light weight and the structural support it provides, however other materials may be used if desired. Additional material may be placed in the lid 11 of case 2 to provide additional protection to the elements of the treatment apparatus.

Template 13 is shown as fully enclosing the cavity defined by body section 10. This is preferred, to maximize the shock absorbing effects of template 13, as well as to allow the size of the case 2 to be minimized. However, other shapes are possible depending upon the application.

The various elements comprising the treatment apparatus are fitted into various openings in the template 13, which openings are preferably closely conformed to the shape of the element to be inserted therein. In this manner, shock absorption is maximized, wasted space is minimized, and a simple means for the patient to determine where each respective element is to be placed within template 13 is provided.

Although it is preferred that the openings in template 13 closely conform to the elements of the system, it is also possible for the elements to be more loosely inserted into those openings. However, it is necessary that at least some restraint in movement be provided so that the various elements will not loosely move about.

Moreover, it is not necessary that a template 13 be used to retain the elements of the system in place. It is also possible to affix the elements to case 2, either directly, or using additional framing members to do so. In such case, any sound insulation which would be provided by template 13 would be sacrificed.

The various elements of the system would then be positioned within the template 13 of case 2. FIG. 1 illustrates one manner in which the various elements of the system can be positioned within case 2. Other orientations for the various elements of the system may also be used.

Compressor 4 may be any compressor which is capable of providing the pressures necessary to properly operate the nebulizer 7. Typically these pressures will be within the range of 4–8 liters/minute. One compressor which has been found to produce excellent results is manufactured by Interdynamics, Corp., Model No. EC-15.

Battery 5, although various batteries may be used, is preferably selected to match the characteristics of compressor 4. For the previously identified compressor 4, a battery such as that manufactured by the Power-Sonic Corp., Model No. 621-0340, has been found to produce excellent results. A fully charged battery of this type is capable of providing up to 120, 10 minute treatments, if used in conjunction with the compressor 4 previously identified, thus providing a more than adequate range to an ambulatory patient before it becomes necessary to recharge the battery 5.

A wide variety of nebulizers 7 may be used in conjunction with the foregoing elements. For example, excellent results have been achieved using a nebulizer such as that manufactured by the Vix Corp., Model No. 51.

Also provided is a quantity of tubing 8, plastic or rubber, which is used to connect the compressor 4 to the nebulizer 7; a mouthpiece 9 which is placed onto the nebulizer 7 to introduce the vaporized medication into the patient 3; and a quantity of medication 14 (use of disposable unit vial containers is illustrated by way of example), for use in the nebulizer 7.

Although a mouthpiece 9 is shown in FIG. 1, it is also possible to provide a facemask for use in conjunction with the system above described, if use of a facemask is either indicated or preferred.

Figure 2:
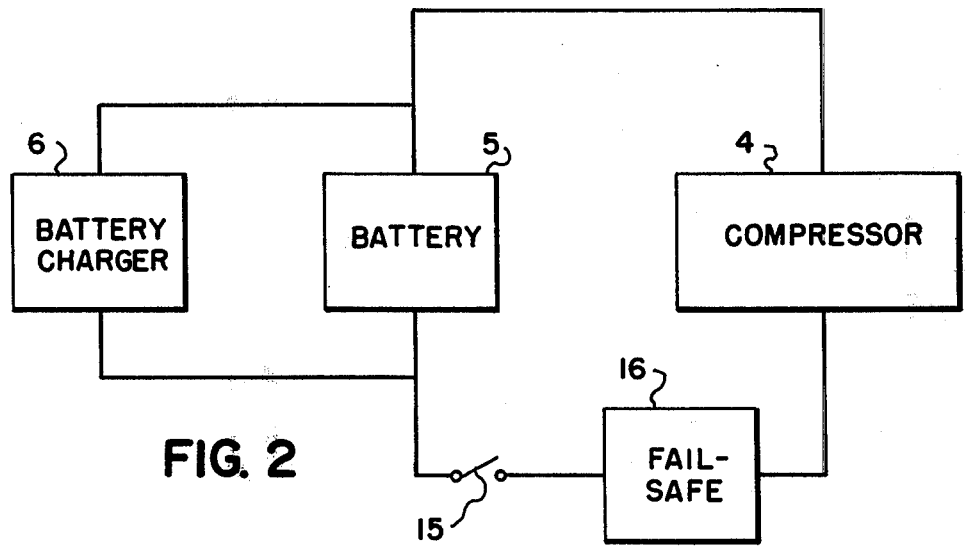
FIG. 2 is a block diagram of the interconnection between the electrical components illustrated in FIG. 1.

The foregoing elements are electrically connected in the manner diagrammatically shown in FIG. 2. Essentially the compressor 4 and battery 5 are directly connected to each other, however interposed between those elements, in series connection, is provided a switch 15 and fail-safe 16.

Switch 15 is used as the master switch which operates the compressor 4 and therefore the treatment apparatus. A single-pole-single-throw switch is adequate for this purpose. As illustrated in FIG. 1, switch 15 extends through case 2, to permit actuation of the switch from outside the case 2.

Although such positioning of the switch 15 is not essential, it is preferred, since a patient carrying the case 2 by handle 12 is able to operate the switch 15 easily and quickly from that position. In fact, a patient is able to switch the apparatus on and off as needed, during movement, without having to adjust or put down the case 2. Available relief is therefore quickly provided. Positioning the switch 15 near the handle 12 also reduces the potential for accidentally turning on the treatment apparatus, which could adversely effect the power available from battery 5 for operation of compressor 4.

Since the apparatus of the present invention is intended for use while a patient is outside, and away from external sources of power, it is essential that the patient be assured that the battery 5 will maintain sufficient power to operate the system as needed. Consequently, in addition to positioning the switch 15 as above described, it is also preferred, although not required, to provide a fail-safe 16 which is capable of preventing unwanted, accidental operation of the compressor 4, which could adversely affect the power available from battery 5.

One example of such a fail-safe 16 is illustrated in FIG. 1. An electrical jack 17 is positioned to extend through case 2 as shown. This jack 17 is placed in series between the battery 5, switch 15 and compressor 4. A plug 18 is also provided which is capable of completing the circuit and thereby permit operation of the treatment apparatus. The terminals of plug 18 are in electrical connection so that inserting the plug 18 into jack 17 completes the circuit of FIG. 2. In this manner, the system can only be operated when plug 18 is in jack 17, irrespective of the positioning of switch 15, preventing unwanted operation of compressor 4.

It is also possible for fail-safe 16 to comprise a locking switch, operated in response to a key, which switch is electrically connected in series between battery 5, switch 15 and compressor 4. Other fail-safe devices may also be used.

Also shown in FIG. 2 is battery charger 6. Such a battery charger could be omitted from the system of the present invention, however its inclusion is preferred so that a means for recharging the battery 5 is always available to the patient. Battery charger 6 is connected to battery 5 in known manner. For safety, this is preferably done via jack 19, which is electrically connected to battery 5. In such case, all that need be done is that battery charger 6 be removed from case 2, connected to a standard A.C. outlet, and connected to jack 19. In this manner, the battery charger may be removed from case 2 and connected for operation, and case 2 may then be closed and locked, to protect its contents, allowing case 2 to sit unattended while the battery 5 is being recharged.

In operation, the apparatus of the present invention is capable of providing a nebulized medication to a patient 3 as follows.

Upon sensing the need for a treatment, patient 3 would open case 2 and remove the nebulizer 7, tubing 8 and mouthpiece 9 therefrom. One end of tubing 8 is connected to compressor 4, by being placed over the outlet 20 of the compressor. The nebulizer 7 is connected to the remaining end of tubing 8. Mouthpiece 9 is connected to the outlet 21 of nebulizer 7. Finally, nebulizer 7 is filled with medication 14. The apparatus is then ready for use.

It is generally preferred that the air supplied by compressor 4 be filtered prior to use in nebulizer 7. Such filtration may be provided internally to compressor 4, or if desired, externally, using an in-line filter 22 such as is illustrated in FIG. 1. A combination of internal and in-line filtration may also be used.

Operation of the apparatus is controlled by switch 15. If fail-safe 16 is made part of the apparatus, this fail-safe 16 would also have to be actuated, to complete the circuit of FIG. 2.

The patient 3 may then proceed with the treatment as needed. This may be done while patient 3 is stationary, or if necessary while the patient 3 is in motion. In the latter event, case 2 may be closed, tubing 8 being permitted to extend through an opening 23 provided in case 2, and operated by switch 15, which is conveniently positioned adjacent to handle 12. In this manner, the apparatus may be carried by patient 3, even during its use. This is permitted by the lightweight construction of the apparatus of the present invention, the weight of which is capable of being maintained at less than 7 pounds.

It is also possible to provide case 2 with a carrying strap, or shoulder strap, which enables case 2 to be carried, while also leaving the hands of the patient 3 free to adjust the apparatus during use as needed.

It may therefore be seen that the above disclosed invention serves well to accomplish the objects previously stated. It may also be seen that the above described invention may be embodied in other specific forms in addition to those above disclosed and therefore the disclosure made should be interpreted in an illustrative and not a limiting sense.

What is claimed is:

1. An apparatus for the treatment of a patient having a respiratory ailment with a medication, which apparatus comprises an outer portable case, said case being provided with a cavity for containing means for supplying a fluid, under pressure, to the patient, the means for supplying a fluid comprising a compressor adapted to supply a fluid;

nebulizing means adapted to contain the medication therein and connected to the compressor to receive fluid therefrom, which fluid is caused to interact with the medication within the nebulizing means, thereby nebulizing the fluid;

means for introducing the nebulized fluid into the patient, which introducing means is connected to the nebulizing means;

electrical circuit means including a battery for operating the compressor, which electrical circuit means is electrically connected to the compressor, a portable fail-safe means comprising a jack portion projecting exteriorly of the case and connected in said electrical circuit means in series between the compressor and the battery and plug means including terminals removably inserted into said jack portion, whereby said battery is connected to said compressor only upon inserting the plug into the jack portion;

the electrical circuit means and the compressor being maintained internal of the case, and portable switching means, mounted externally to the case, which switching means controls operation of the compressor;

wherein the nebulizing means and the introducing means are internal of the case when not in use, and are external of the case when in use whereby the apparatus is capable of being carried and operated during ambulatory periods of the patient, and during ambulation of that patient.

2. The apparatus of claim 1 which further comprises filtration means positioned between the compressor and the nebulizing means.

3. The apparatus of claim 1 wherein the fluid is air.

4. The apparatus of claim 3 wherein the quantity of the fluid supplied by the fluid supplying means is within the range of 4–8 liters per minute.

5. The apparatus of claim 1 which further comprises means for recharging the battery, which recharging means is connectable to the battery when the case is closed.

6. The apparatus of claim 1 and a template enclosing the said cavity of the outer case, the template being provided with a plurality of openings to contain at least some of the said components comprising the means for supplying a fluid.

7. The apparatus of claim 6 wherein each said opening is configured to closely conform to the shape of the component contained therein whereby a shock absorbing effect can be realized to thereby protect the said components while the apparatus is being carried.

* * * * *